United States Patent
Boese et al.

(10) Patent No.: US 8,583,214 B2
(45) Date of Patent: Nov. 12, 2013

(54) METHOD FOR VISUALLY SUPPORTING AN INVASIVE EXAMINATION OR THERAPY OF THE HEART WITH THE AID OF AN INVASIVE INSTRUMENT

(75) Inventors: Jan Boese, Eckental (DE); Norbert Rahn, Forchheim (DE)

(73) Assignee: Siemens Aktiengesellschaft, München (DE)

( * ) Notice: Subject to any disclaimer, the term of this patent is extended or adjusted under 35 U.S.C. 154(b) by 2017 days.

(21) Appl. No.: 11/524,611

(22) Filed: Sep. 21, 2006

(65) Prior Publication Data
US 2007/0083108 A1 Apr. 12, 2007

(30) Foreign Application Priority Data
Sep. 21, 2005 (DE) .......................... 10 2005 045 073

(51) Int. Cl.
 A61B 5/055 (2006.01)
 A61B 8/00 (2006.01)
(52) U.S. Cl.
 USPC ........... 600/424; 600/411; 600/413; 600/427; 600/439
(58) Field of Classification Search
 None
 See application file for complete search history.

(56) References Cited

U.S. PATENT DOCUMENTS

| | | | |
|---|---|---|---|
| 5,211,165 A | 5/1993 | Darrow | |
| 5,437,277 A * | 8/1995 | Dumoulin et al. | 600/424 |
| 6,368,285 B1 | 4/2002 | Osadchy et al. | |
| 6,925,319 B2 * | 8/2005 | McKinnon | 600/407 |
| 6,957,098 B1 * | 10/2005 | Hyde et al. | 600/424 |
| 2001/0035871 A1 * | 11/2001 | Bieger et al. | 345/630 |
| 2003/0220561 A1 * | 11/2003 | Camus et al. | 600/424 |
| 2004/0077942 A1 | 4/2004 | Hall et al. | |
| 2005/0004449 A1 | 1/2005 | Mitschke et al. | |
| 2005/0090743 A1 | 4/2005 | Kawashima et al. | |
| 2006/0067459 A1 | 3/2006 | Boese et al. | |
| 2006/0100505 A1 * | 5/2006 | Viswanathan | 600/424 |
| 2007/0078325 A1 * | 4/2007 | Fuimaono et al. | 600/407 |

FOREIGN PATENT DOCUMENTS

| | | |
|---|---|---|
| DE | 102 10 645 A1 | 10/2003 |
| DE | 103 22 739 A1 | 12/2004 |
| DE | 103 40 544 A1 | 3/2005 |
| DE | 10 2004 048 209 B3 | 9/2005 |

(Continued)

OTHER PUBLICATIONS

Communication from Japanese Patent Office stating cited reference, Feb. 2, 2012, pp. 1-3.

*Primary Examiner* — Long V. Le
*Assistant Examiner* — Angela M Hoffa

(57) ABSTRACT

To visually support a catheter ablation in the heart, three-dimensional image data have been used prior to the intervention. During ablation, the position of the catheter is pinpointed by an orientation system. The orientation system acquires electroanatomical 3D mapping data. The two-dimensional image data is assigned to the 3D mapping data in the correct position and dimensions which is a time-consuming step. The invention makes provision for the orientation system being in a fixed location relative to the X-ray system so that a positionally and dimensionally correct alignment of the X-ray image data set with the 3D mapping data is no longer required. An image or surface based 3D-3D alignment of the three-dimensional data acquired prior to the intervention with the three-dimensional X-ray image data is considerably less time-consuming than alignment thereof with the 3D mapping data and is more reliable because more structures is recognized in the three-dimensional X-ray image data.

15 Claims, 1 Drawing Sheet

(56) References Cited

FOREIGN PATENT DOCUMENTS

| | | |
|---|---|---|
| EP | 1 504 713 A1 | 2/2005 |
| JP | 2002153443 A | 5/2002 |
| JP | 2002315754 A | 10/2002 |
| JP | 2003180680 A | 7/2003 |
| JP | 2004533863 A | 11/2004 |
| WO | WO 2004021910 A1 | 3/2004 |
| WO | WO 2005/027765 A1 | 3/2005 |
| WO | WO 2005070318 A1 | 8/2005 |
| WO | WO 2005084122 A2 | 9/2005 |

* cited by examiner

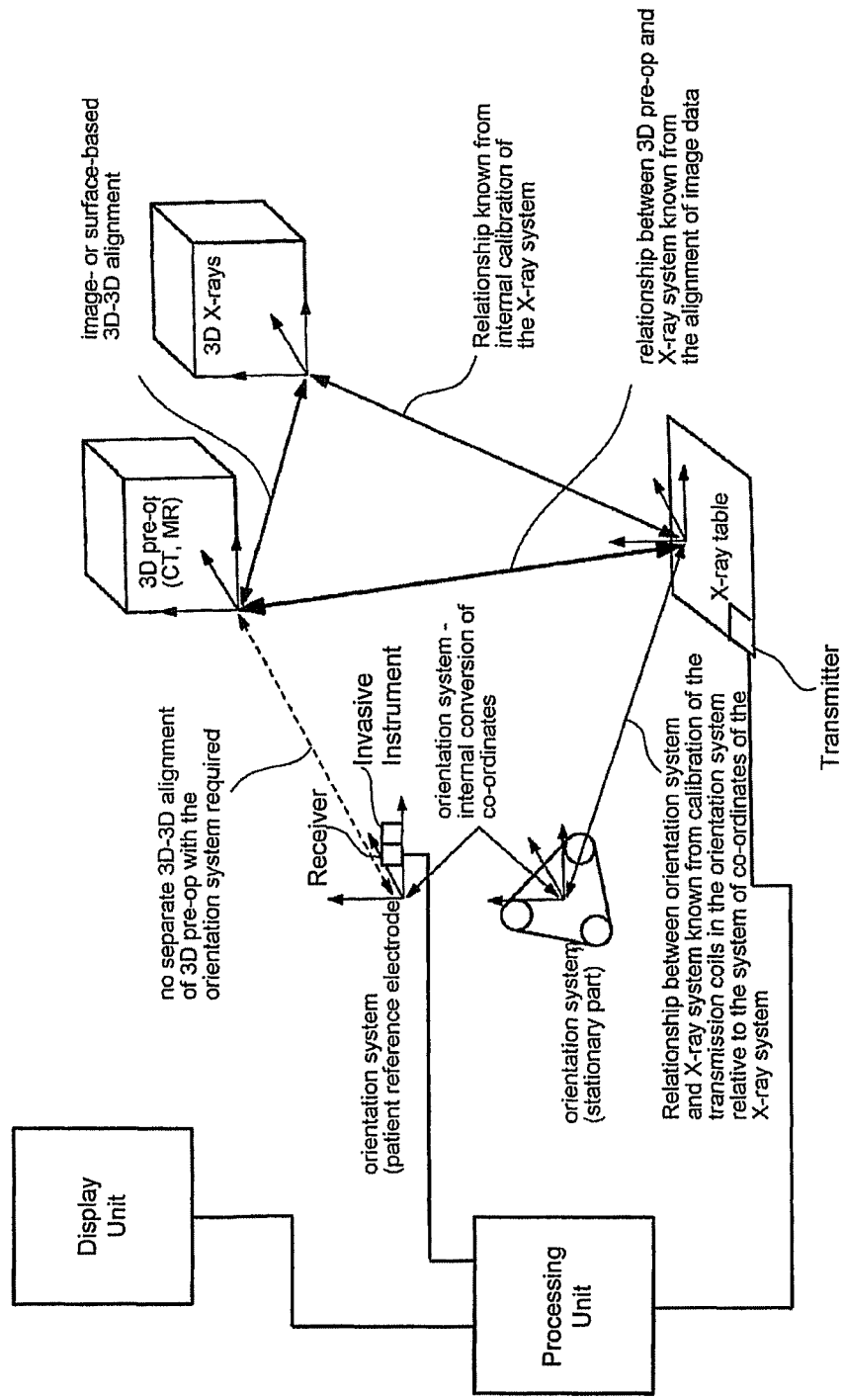

METHOD FOR VISUALLY SUPPORTING AN INVASIVE EXAMINATION OR THERAPY OF THE HEART WITH THE AID OF AN INVASIVE INSTRUMENT

CROSS REFERENCE TO RELATED APPLICATIONS

This application claims priority of German application No. 10 2005 045 073.3 filed Sep. 21, 2005, which is incorporated by reference herein in its entirety.

FIELD OF THE INVENTION

The invention relates to a method for visually supporting an invasive examination or therapy of the heart with the aid of an invasive instrument.

BACKGROUND OF THE INVENTION

The therapies involved are mainly those of the ablation kind with the aid of an ablation catheter. For the therapy of atrial fibrillation in the heart, for example, the pulmonary veins of the atrium are electrically isolated by annular ablations around the pulmonary veins. The procedure for carrying out annular ablation is very complex.

Arrythmias in ventricular movement (ventricular fibrillation) can result from scar tissue in the myocardium. This scar tissue forms as a result of an infarction, for example. An accurately targeted ablation on the scar tissue may suppress the ventricular fibrillation. Here, too, ablation is very difficult to carry out because of the requirement for accurate targeting.

Hitherto, two kinds of image data have been used for visually supporting an invasive therapy of the heart with the aid of an ablation catheter:

Firstly, three-dimensional image data acquired prior to the actual operation are used. In these three-dimensional image data the areas requiring ablation can be recognized. The problem lies in aligning three-dimensional image data with the position of the ablation catheter.

Orientation systems provided on the ablation catheter, such as the CARTO system from Biosense Webster, for example, are usually used, optionally with the assistance of a further catheter. Electro-anatomical maps can be produced with the aid of these systems, the maps essentially being a representation in image form of electrophysiological cardiac signals as a function of the position of a signal recorder.

The maps can also be used effectively during ablation.

In order to be able to use the three-dimensional image data that have been acquired prior to therapy at the same time as the maps, registration of three-dimensional image data with electroanatomical maps can be carried out. "Registration" is understood here to mean that electroanatomical 3D mapping data can be aligned with the 3D image data in the correct position and dimensions, that is, that the systems of co-ordinates are combined with each other. This is disclosed, for example, in DE 103 405 44 A1.

Aligning 3D mapping data with one another in the correct position and dimension is very time-consuming, however.

A registration is also carried out in a method known from DE 102 10 645 A1 for detecting and imaging a medical catheter inserted in an area of a patient to be examined. There is a position-detecting means on the medical catheter, the means being part of a position-detection system, and the system of co-ordinates of the position-detection system is registered with the system of co-ordinates of a 3D construction image produced with the aid of an X-ray C-arm. This allows the tip of the catheter to be displayed in the 3D reconstruction image on a monitor.

EP 1 504 713 A1 discloses a navigation system for cardiac therapies, in which a medical catheter is equipped with electromagnetic coils as sensors for a navigation system.

SUMMARY OF THE INVENTION

The invention addresses the problem of avoiding a time-consuming registration process at least in a first step.

To solve the problem, two methods according to the claims are provided.

The methods have in common the feature that three-dimensional image data are recorded, the co-ordinates of which in relation to an orientation system are already known from the outset. When an X-ray system is used, the transmission coils of the orientation system are affixed in a fixed location in the X-ray system. When an ultrasound image generation system is used, the same transmission coils are also used for orienting the ultrasound transducer or at least such transmission coils that have a fixed location with respect to the other transmission coils. Because of the fact that the co-ordinates of the data captured using the X-ray system or the ultrasound image-generation system are known from the outset, the co-ordinates of the invasive instrument can be determined with the aid of the orientation system and then be visualized in the three-dimensional image data set (in the X-ray image data set or in the ultrasound image data set), a preferably symbolic image of the invasive instrument being made to appear, or viewed through the invasive instrument.

According to a first variant, the method according to the invention for visually supporting an invasive support (sic) or examination of the heart with the aid of an instrument therefore comprises the following steps:

a) an X-ray system with the aid of which three-dimensional X-ray image data of the heart are obtainable is provided,
b) an orientation system is provided in a fixed location with respect to the X-ray system, the orientation system being designed such that by means of a transmitter affixed to the X-ray system, which transmitter transmits radio waves and by means of a receiver affixed to the invasive instrument, it can determine the position of the instrument relative to the transmitter and thus without any registration with respect to the X-ray system.
c) a three-dimensional X-ray image data set of the heart is produced with the aid of the X-ray system.
d) the co-ordinates of the invasive instrument are determined with the aid of the orientation system and
e) a visualization of the three-dimensional X-ray image data set is achieved on a screen, a preferably symbolic image of the invasive instrument being made to appear, or viewed through the invasive instrument.

Steps d) and e) can preferably be repeated during the examination or therapy, that is, the visualization is subsequently transmitted to the invasive instrument (the ablation catheter). As a result thereof, the physician can make maximum use of the visualization when carrying out the therapy.

Step c) can also be repeated as required in order to update the three-dimensional image of the heart.

The invention makes use of the fact that new technologies allow three-dimensional imaging of the heart, as disclosed in DE 10 2004 048 209 B3, for example.

Here the three-dimensional X-ray image data set is captured using ECG gating. In ECG gating, an ECG is taken at the time the X-ray images are taken. Information is obtained as to which X-ray image was taken during which phase of the cardiac cycle. The X-ray images are then aligned with particular phases in the cardiac cycle, it being optionally possible to correct the individual X-ray images mathematically in order to allow mapping onto another phase in the cardiac cycle.

In a preferred embodiment of the invention, the three-dimensional X-ray image data set is aligned with a particular phase in the cardiac cycle, and, with the aid of the X-ray system, a further three-dimensional X-ray image data set is generated, which is aligned with a different phase in the cardiac cycle. In each case, a visualization is then achieved, the visualizations preferably offering a unified representation of the data by means of spatial or temporal combination thereof. For example, there can be a plurality of screens in succession each showing a two-dimensional visualization of an image data set, corresponding on the respective screen with a particular phase in the cardiac cycle. In particular, for "endoscopic views" of the three-dimensional image data set, there is also the option of displaying on the screen various images that are aligned with various phases in the cardiac cycle at consecutive points in time (e.g. displaying oscillating images).

The invention acquires the three-dimensional X-ray image data, in order to avoid having to register the image data acquired prior to therapy with 3D mapping data. However, this does not conflict with there being an embodiment in which a three-dimensional pre-operative image data set is acquired prior to the examination or therapy by means of an image generation system that is different from the X-ray system (e.g. a computer tomography (CT) system, a magnetic resonance imaging (MRI) system, an ultrasound system, a positron emission tomography (PET) or a single positron emission computer tomography (SPECT) system). This pre-operative image data set can be aligned with the X-ray image data set in the correct position and dimensions (that is, registered therewith), as a result of which the instrument's position that has been pinpointed is provided as a coordinate in the pre-operative image data set. Instead of visualizing the X-ray image data set or in addition thereto or even superimposed with the visualization of the X-ray image data set, a visualization of the pre-operative image data set can be achieved on a screen with a preferably symbolic image of the invasive instrument being made to appear or viewed through the viewpoint of the invasive instrument (endoscopic view, for example). In this embodiment, the pre-operative image data set is therefore not aligned in the correct position and dimensions with a mapping image data set but with the X-ray image data set. As a result of the similarities in the images, this is a considerably more simple step than the corresponding alignment of image data sets with a map.

The pre-operative image data set can also be acquired using ECG gating, the X-ray image data set and the pre-operative image data set preferably being aligned with the same phase in the cardiac cycle. This makes it easier to align the images with one another.

Since both the X-ray image data set and the pre-operative image data set are both in a known relationship with the orientation system following the positionally and dimensionally accurate alignment thereof with the X-ray image data set, the mapping image can also be incorporated in the visualization. This means that on the invasive instrument a measuring device is provided for the electrophysiological detection of cardiac signals, said device allowing the cardiac signals to be combined, using the orientation system, into electroanatomical maps having coordinates that are permanently aligned with the orientation system and hence with the X-ray system, said maps being shown superimposed on or made to appear in the respective visualization (that is, in the visualization of the X-ray image data set or of the pre-operative image data set or of a superimposition of the two).

In the superimposition of images that has been referred to on several occasions above, superimposition techniques according to the prior art are used. In particular, a superimposition can take place such that a user or a user input can alternate between two forms of imaging, one form of imaging being based primarily on the first superimposed image and the other form of imaging on the second superimposed image.

BRIEF DESCRIPTION OF THE DRAWINGS

A preferred embodiment of the invention is now described with reference to the drawing in which the figure shows the spatial relationships between the systems of co-ordinates when acquiring images using different image-generation methods.

DETAILED DESCRIPTION OF THE INVENTION

The figure shows three different systems for obtaining data to support a therapy of the heart, such as an ablation. Prior to the actual therapy, a three-dimensional image data set "3D pre-op" is acquired by means of computer tomography (CT) or magnetic resonance (MR). The system of co-ordinates is not at first correlated with other systems of co-ordinates. Furthermore, prior to or during therapy, a three-dimensional X-ray image data set of the heart is acquired using a technique as described in German patent application 10 2004 048209.8. The relationship between the system of co-ordinates of the three-dimensional X-ray image data set "3D X-rays" and an X-ray table on which the patient is lying, is known from the internal calibration within the X-ray system. The therapy of the heart ensues in particular with the aid of a catheter, for example an ablation catheter. An orientation system is available to pinpoint the position of the catheter. The orientation system comprises a stationary component, that is, transmission coils which are arranged in a fixed location with respect to the X-ray table, and also a receiver on a patient reference electrode on the catheter. In other words, the relationship between the orientation system and the X-ray system is known by calibrating the orientation system's transmission coils relative to the X-ray system's system of co-ordinates. An internal transformation of the co-ordinates from the transmitter to the receiver takes place within the orientation system. 3D mapping images can be generated with the aid of the orientation system's moving part. These are based on electrophysiological measurements made by the patient reference electrode, which are aligned with the location that has been pinpointed for the electrode in the mapping image.

There then ensues as a single necessary alignment step, an image or surface-based 3D-3D alignment (registration) of the 3D pre-op data with the 3D X-ray data. In the context of this alignment, similarity calibrations are used to determine how the systems of co-ordinates "3D pre-op" and "3D X-ray" are to be imaged one over the other.

Once this alignment of data has been achieved, a separate 3D—3D alignment of 3D pre-op data with the orientation system is not necessary (see dotted arrow). As a result of the fact that the relationship between the system of co-ordinates of 3D X-ray data and the X-ray table and between the orientation system and the X-ray table is known in each case, the relationship of 3D pre-op data to the X-ray table and hence to the orientation system is also known as a result of the alignment of 3D pre-op data with 3D X-ray data.

The invention is based on the fact that a three-dimensional X-ray image data set of 3D X-rays is acquired, the relationship whereof is in a fixed location with respect to the orientation system, the 3D X-ray image data allowing alignment with the data acquired pre-operatively, 3D pre-op, to be carried out in a relatively simple manner because corresponding structures can be recognized on the images such that a time-consuming alignment of pre-operative data 3D pre-op with the orientation system as in the prior art is no longer required.

As a result of the fact that the relationships are known between the two three-dimensional image data sets, 3D pre-op and 3D X-rays and finally also those with the orientation system, that is with 3D mapping data, the two image data sets and the mapping data can be visualized together in any combinations on an X-ray image. It is thus possible once the catheter has been pinpointed to make it appear either into the three-dimensional X-ray image data or into the three-dimensional pre-operatively acquired data. It is also possible to display the mapping data superimposed with the other image data. The superimposed image can, for example, be such that the pre-operatively acquired data are displayed and the position of the ablation catheter is shown therein. By activating the mouse or a key, the view can change to show the 3D mapping data.

Consequently, the operator directing the ablation catheter is provided with a wide variety of imaging options, the essential point being that firstly he has image data, and secondly is provided with the position of the catheter by means of the orientation system. Thus he can orient himself in the image data during the operation. The new current position of the ablation catheter is regularly determined by means of the orientation system. The visualization is updated accordingly, that is, the imaging of the three-dimensional image data moves during the insertion of the ablation catheter so that the doctor providing the treatment can orient himself to a certain extent in a virtual world in order to carry out the ablation as accurately as possible. This is useful both in therapies for atrial fibrillation, in which the pulmonary veins have to be ablated at precisely determined points, and in therapy for ventricular fibrillation, in which ablation has to be performed in the vicinity of scar tissue or along the scar tissue. In the latter case, the image data set 3D pre-op can be selected in a skilful manner such that the scars are displayed. The scars do not necessarily have to be visible in the 3D X-ray image because the image- or surface-based 3D—3D alignment is sufficiently precise as it is. The scars can be visualized on a screen and the catheter can be directed in an accurately targeted manner.

The invention thus allows a hitherto unknown precision in certain ablation procedures.

The invention claimed is:

1. A method for displaying an invasive instrument during an invasive examination of a heart of a patient, comprising:
   providing an X-ray system;
   arranging an orientation system for the invasive instrument in a fixed location relative to the X-ray system, the orientation system:
      transmitting a radio wave from a transmitter affixed to the X-ray system,
      receiving the radio wave from a receiver affixed to the invasive instrument,
      calibrating a relationship between the X-ray system and the orientation system, based on determining a distance between the X-ray system and the fixed location within the orientation system,
      determining a position of the receiver of the invasive instrument relative to the transmitter of the X-ray system, based on the transmitting, receiving and calibrating steps, without a registration relative to the X-ray system;
   generating a three-dimensional X-ray image data set of the heart with the X-ray image;
   determining a coordinate of the invasive instrument relative to a coordinate of the X-ray system via the orientation system;
   displaying the three-dimensional X-ray image data set with the invasive instrument being visible in the X-ray image data set on a screen;
   wherein a three-dimensional pre-operative image data set is acquired prior to the examination by an image system that is different from the X-ray system;
   and wherein the pre-operative image data set is aligned with the X-ray image data set in a correct position and dimension based on a position of the invasive instrument in a coordinate of the pre-operative image data set.

2. The method as claimed in claim 1, wherein the invasive instrument is displayed as a symbolic image of the invasive instrument.

3. The method as claimed in claim 1, wherein the three-dimensional X-ray image data set is viewed using the invasive instrument.

4. The method as claimed in claim 1, wherein the steps of determining and displaying are repeated during the examination.

5. The method as claimed in claim 1, wherein the generating step is repeated during the examination.

6. The method as claimed in claim 1, wherein the three-dimensional X-ray image data set is generated using ECG gating.

7. The method as claimed in claim 6, wherein the three-dimensional X-ray image data set is aligned with a particular phase in a cardiac cycle and is displayed on the screen.

8. The method as claimed in claim 7, wherein a further three-dimensional X-ray image data set is generated with the X-ray system and aligned with a different phase in the cardiac cycle and displayed on the screen.

9. The method as claimed in claim 8, wherein the three-dimensional X-ray image data set and the further three-dimensional X-ray image data set are spatially or temporally combined to a unified image data and the unified image data is displayed on the screen.

10. The method as claimed in claim 1, wherein the pre-operative image data set is displayed on the screen with the invasive instrument represented by a symbolic image.

11. The method as claimed in claim 10, wherein the pre-operative image data set is viewed on the screen using the invasive instrument.

12. The method as claimed in claim 1, wherein the pre-operative image data set is acquired by a system selected from the group consisting of: a computer tomography system, a magnetic resonance imaging system, an ultrasound system, a positron emission tomography system, and a single positron emission computer tomography system.

13. The method as claimed in claim 1, wherein the pre-operative image data set is acquired using ECG gating, and the X-ray image data set and the pre-operative image data set are aligned with an identical phase in a cardiac cycle.

14. The method as claimed in claim 1, wherein the invasive instrument comprises a measurement device which determines a cardiac signal and the cardiac signal is combined into an electro-anatomical map which is aligned with the orientation system and the map is displayed on the screen.

15. A device for displaying an invasive instrument during an invasive therapy of a patient, comprising:

an X-ray system which generates a three-dimensional image data set of the patient;

an orientation system for the invasive instrument in a fixed location relative to the X-ray system, the orientation system comprising:

a transmitter affixed to the X-ray system which transmits a wave signal, a receiver affixed to the invasive instrument which receives the wave signal, a processing unit which is configured to calibrate a relationship between the X-ray system and the orientation system, based on a determined distance between the X-ray system and the fixed location within the orientation system; said processing unit being further configured to determine a coordinate of the invasive instrument relative to a coordinate of the X-ray system, based on the transmitted wave signal, received wave signal, and calibrated relationship, without a registration; and a display unit which displays the three-dimensional image data set with the invasive instrument being visible in the three-dimensional image data set.

* * * * *